(12) United States Patent
Kuriger et al.

(10) Patent No.: US 7,552,843 B2
(45) Date of Patent: Jun. 30, 2009

(54) CARTRIDGE WITH A WHEEL FOR SEALING THE OPENING

(75) Inventors: Rex J. Kuriger, Granger, IN (US); Tieming Ruan, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/885,911

(22) PCT Filed: Mar. 22, 2006

(86) PCT No.: PCT/US2006/010310

§ 371 (c)(1),
(2), (4) Date: Sep. 7, 2007

(87) PCT Pub. No.: WO2007/024272

PCT Pub. Date: Mar. 1, 2007

(65) Prior Publication Data

US 2008/0164280 A1    Jul. 10, 2008

Related U.S. Application Data

(60) Provisional application No. 60/663,781, filed on Mar. 22, 2005.

(51) Int. Cl.
*B65G 59/00* (2006.01)

(52) U.S. Cl. ................ 221/228; 221/208; 221/224; 221/210; 221/235

(58) Field of Classification Search .......... 221/1–312 C
See application file for complete search history.

(56) References Cited

U.S. PATENT DOCUMENTS 4,911,344 A    3/1990    Kahler .................. 221/135

(Continued)

FOREIGN PATENT DOCUMENTS

EP    1 321 769 A1    6/2003

(Continued)

OTHER PUBLICATIONS

Written Opinion of the International Searching Authority corresponding to co-pending International Patent Application No. PCT/US2006/010310, European Patent Office, dated Mar. 13, 2007, 6 pages.

(Continued)

*Primary Examiner*—Gene Crawford
*Assistant Examiner*—Michael K Collins
(74) *Attorney, Agent, or Firm*—Nixon Peabody LLP (57) ABSTRACT

A dispensing mechanism is adapted to eject a test sensor from a cartridge opening formed in a cartridge containing test sensors. The dispensing mechanism comprises a gear rack, a gear, and a wheel. The gear rack includes a first portion and a second portion located generally parallel to one another. The second portion of the gear rack includes a first plurality of teeth. The gear includes a second plurality of teeth that are adapted to be engaged by the first plurality of teeth upon movement of the gear rack. The wheel is operatively engaged by the gear and is adapted to dispense the test sensor from the cartridge opening and to seal the cartridge opening. The movement of the gear rack in a first direction causes the gear to rotate causing the wheel to rotate. The rotation of the wheel dispenses the test sensor through the cartridge opening.

28 Claims, 9 Drawing Sheets

U.S. PATENT DOCUMENTS

| | | | |
|---|---|---|---|
| 5,383,569 A * | 1/1995 | Muto | 221/203 |
| 5,513,773 A * | 5/1996 | Cargill | 221/231 |
| 5,906,366 A * | 5/1999 | Chang | 271/124 |
| 5,941,414 A * | 8/1999 | Kasper | 221/210 |
| 6,534,017 B1 | 3/2003 | Bottwein et al. | 422/104 |
| 6,827,899 B2 | 12/2004 | Maisey et al. | 422/61 |
| 6,908,008 B2 * | 6/2005 | Pugh | 221/135 |
| 6,997,343 B2 * | 2/2006 | May et al. | 221/232 |
| 7,138,089 B2 * | 11/2006 | Aitken et al. | 422/82.01 |
| 7,419,154 B2 * | 9/2008 | Pelletier et al. | 271/124 |
| 2003/0036200 A1 | 2/2003 | Charlton | 436/43 |
| 2003/0089730 A1 | 5/2003 | May et al. | 221/232 |
| 2003/0191415 A1 | 10/2003 | Moerman et al. | 600/584 |
| 2007/0215634 A1 * | 9/2007 | Levin | 221/231 |
| 2007/0293790 A1 * | 12/2007 | Bainczyk et al. | 600/583 |
| 2008/0181818 A1 * | 7/2008 | Ruan | 422/68.1 |

FOREIGN PATENT DOCUMENTS

| | | |
|---|---|---|
| EP | 1 500 925 A1 | 1/2005 |
| GB | 2 388 898 A | 11/2003 |
| JP | 9250998 | 9/1997 |
| WO | WO 02/078533 A2 | 10/2002 |
| WO | WO 03/082091 A2 | 10/2003 |
| WO | WO 03/082092 A1 | 10/2003 |
| WO | WO 03/083469 A2 | 10/2003 |

OTHER PUBLICATIONS

International Search Report corresponding to co-pending International Patent Application No. PCT/US2006/010310, European Patent Office, dated Mar. 13, 2007, 5 pages.

* cited by examiner

CARTRIDGE WITH A WHEEL FOR SEALING THE OPENING

CROSS-REFERENCE TO RELATED APPLICATIONS

This application claims priority to Application No. 60/663,781 filed on Mar. 22, 2005, which is incorporated by reference in its entirety.

FIELD OF THE INVENTION

The present invention relates generally to test-sensor dispensing devices and, more particularly, to a test-sensor cartridge having an integrated sealing and dispensing wheel.

BACKGROUND OF THE INVENTION

Test sensors (e.g., biosensors) containing reagents are often used in assays for determining the analyte concentration in a fluid sample. The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. Each test requires that a new test sensor be used, and thus, a number of test sensors may be used in a single day. Cartridges that contain a number of test sensors are used to allow users to carry multiple sensors around within a single object. The cartridge may utilize a drum or a disk to store the test sensors individually, or the cartridge may contain a plurality of stacked sensors. These cartridges may then be incorporated directly into a meter.

The reagents used to assist with the determination of the analyte concentration are typically sensitive to water and deteriorate if exposed for a period of time. Desiccants are utilized to minimize the exposure of the reactants to water and water vapor. To maintain the desiccant over time, the desiccant must be sealed off from the external atmosphere. In a drum or a disk cartridge, the test sensors are stored in individual compartments and both a sensor and a desiccant are sealed in the compartment. However, these types of cartridges typically result in low space efficiency and a higher cost for sealing each of the plurality of individual compartments.

In a cartridge containing stacked sensors, a separate desiccation chamber is provided that contains a desiccant for desiccating the entire cartridge. To maintain the desiccant, each of the openings to the cartridge is generally sealed. However, for a test sensor to be dispensed, at least one of the seals must be opened to allow a test sensor to exit the cartridge. In cartridges where foil is used to seal the openings, once the first test sensor has been dispensed, it is typical for the cartridge to remain exposed. In other stacked-sensor cartridges, the slot from which the test sensor is ejected is resealable, but at least a second opening is required through the cartridge to allow an ejection mechanism to eject the test sensor. This second opening may increase the potential for exposure of both the reagents and the desiccant to the external environment.

Thus, there exists a need for an improved test-sensor cartridge for efficiently storing and maintaining test sensors.

SUMMARY OF THE INVENTION

According to one embodiment of the present invention a dispensing mechanism for ejecting a test sensor from a cartridge opening formed in a cartridge containing a plurality of test sensors is disclosed. The dispensing mechanism comprises a gear rack, a gear, and a wheel. The gear rack includes a first portion and a second portion located generally parallel to one another. The second portion of the gear rack includes a first plurality of teeth. The gear includes a second plurality of teeth that is adapted to be engaged by the first plurality of teeth upon movement of the gear rack. The wheel is operatively engaged by the gear and is adapted to dispense the test sensor from the cartridge opening and seal the cartridge opening. The movement of the gear rack in a first direction causes the gear to rotate causing the wheel to rotate. The rotation of the wheel dispenses the test sensor through the cartridge opening.

According to another embodiment of the present invention, the gear rack of the above-disclosed dispensing mechanism includes a plurality of first portions and a plurality of second portions.

According to yet another embodiment of the present invention a cartridge is disclosed. The cartridge comprises a plurality of walls, a dispensing mechanism, a retention plate, and a spring mechanism. The plurality of walls forms at least one cavity therein. The cavity is adapted to contain a plurality of test sensors. The plurality of test sensors is adapted to assist in the determination of a concentration of an analyte in a fluid sample. At least one of the plurality of walls has an opening adapted to allow a test sensor to be dispensed therefrom. The dispensing mechanism is adapted to dispense a test sensor through the opening. The dispensing mechanism includes (i) a gear rack including a first portion and a second portion located generally parallel to one another, the first portion of the gear rack including a first plurality of teeth, (ii) a gear including a second plurality of teeth, the second plurality of teeth being adapted to be engaged by the first plurality of teeth upon movement of the gear rack, and (iii) a wheel operatively engaged by the gear, the wheel being adapted to dispense the test sensor from the opening and to seal the opening. The retention plate is located in the at least one cavity and is adapted to engage at least one of the plurality of test sensors. The spring mechanism is adapted to engage the retention plate and exert a force on the retention place in the direction of the wheel. The spring mechanism and the retention plate force at least one of the test sensors into contact with a portion of the wheel of the dispensing mechanism.

According to still another embodiment of the present invention, the gear rack included in the dispensing mechanism of the above-described cartridge includes a plurality of first portions and a plurality of second portions.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a test-sensor cartridge having an integrated sealing and dispensing wheel. The cartridge may be used to store a plurality of test sensors in a desiccated state therein. A dispensed test sensor, in conjunction with a meter or instrument, may be used to determine concentrations of at least one analyte in a fluid sample applied to the test sensor. Analytes that may be measured utilizing test sensors include glucose, lipid profiles (e.g., cholesterol, triglycerides, LDL and HDL), microalbumin, hemoglobin $A_{1C}$, fructose, lactate, bilirubin, or prothrombin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, or other (non-body) fluid samples. As used within this application, the term "concentration" refers to an analyte concentration, activity (e.g., enzymes and electrolytes), titers (e.g., antibodies), or any other measure concentration used to measure the desired analyte.

Figure 1:
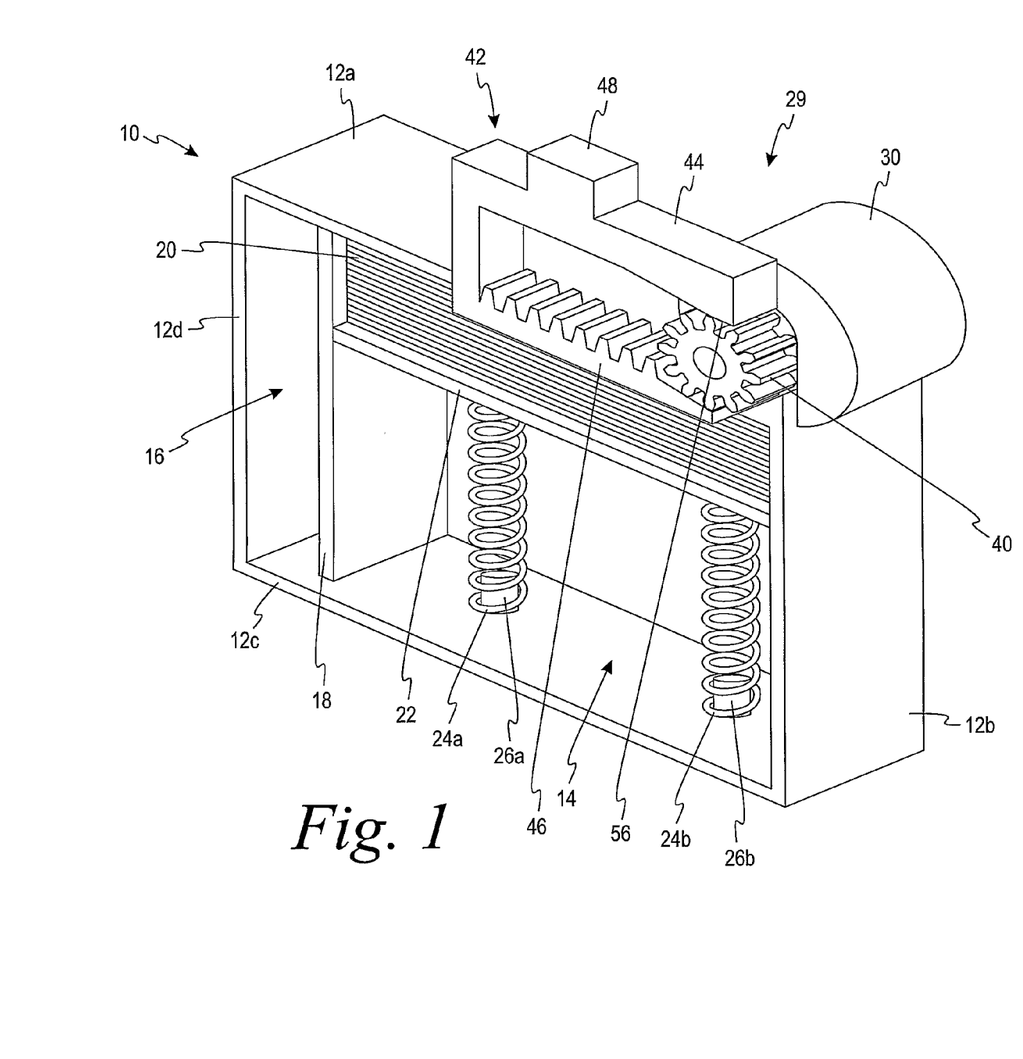
FIG. 1 is a perspective view of a cartridge adapted to contain and dispense a plurality of test sensors, according to one embodiment of the present invention.

Turning now to the drawings and initially to FIG. 1, a test-sensor cartridge 10 is illustrated, according to one embodiment of the present invention. The cartridge 10 includes a plurality of walls 12a-d that forms a central cavity 14 and a desiccant cavity 16. A divide 18 partially separates the central cavity 14 from the desiccant cavity 16. The desiccant cavity 16 is adapted to contain a desiccant while the central cavity 14 is adapted to contain a plurality of test sensors 20 therein. The divide 18 is narrower than the walls 12a-d to allow the cavities 14,16 to be in communication with one another. The desiccant cavity 16 is in communication with the central cavity 14 to allow the desiccant to desiccate the central cavity 14.

The central cavity 14 contains a retention plate 22 that is adapted to engage a test sensor 20. A spring mechanism 23 is located between the retention plate 22 and the wall 12c so as to cause the retention plate 22 to engage the test sensors 20 and bring them proximate to the interior surface (not shown) of the wall 12a. The spring mechanism 23 may be any type of spring, multiple spring, or other device capable of exerting a sufficient force onto the retention plate 22. For example, as illustrated in FIG. 1, a plurality of springs 24a,b are contained in the central cavity 14 and engage both the retention plate 22 and the wall 12c. The springs 24a,b may be attached to the retention plate 22 and the wall 12c. Alternatively, a plurality of posts 26a,b may extend from each surface into a central channel of the springs 24a,b, as illustrated in FIG. 1. The posts 26a-b extend from the wall 12c while a second set of posts (not shown) extend from the retention plate 22, opposite the posts 26a,b. The springs 24a,b exert a force on the retention plate 22 in the direction of the wall 12a. This force causes the retention plate 22 to engage the test sensors 20 and bring them proximate to the interior surface (not shown) of the wall 12a.

Figure 2:
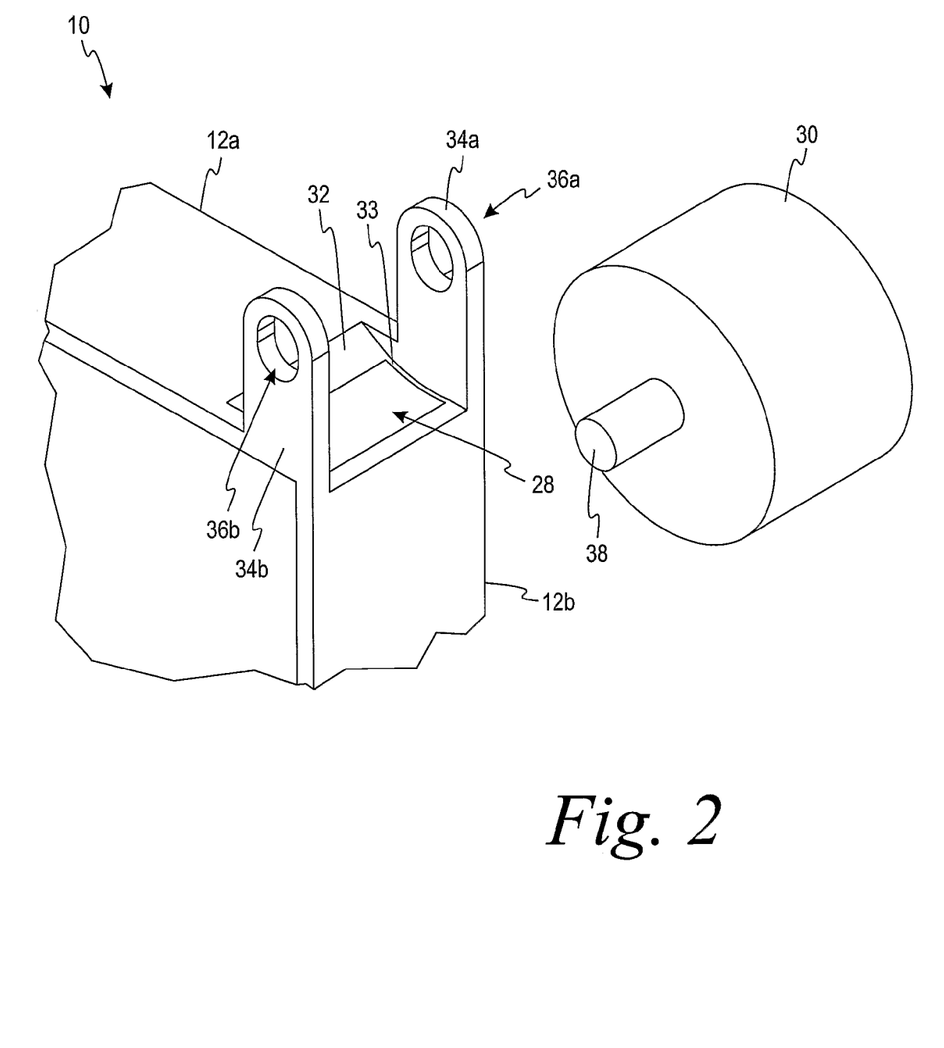
FIG. 2 is a perspective view of a wheel and portion of the cartridge of FIG. 1.
Figure 4A:
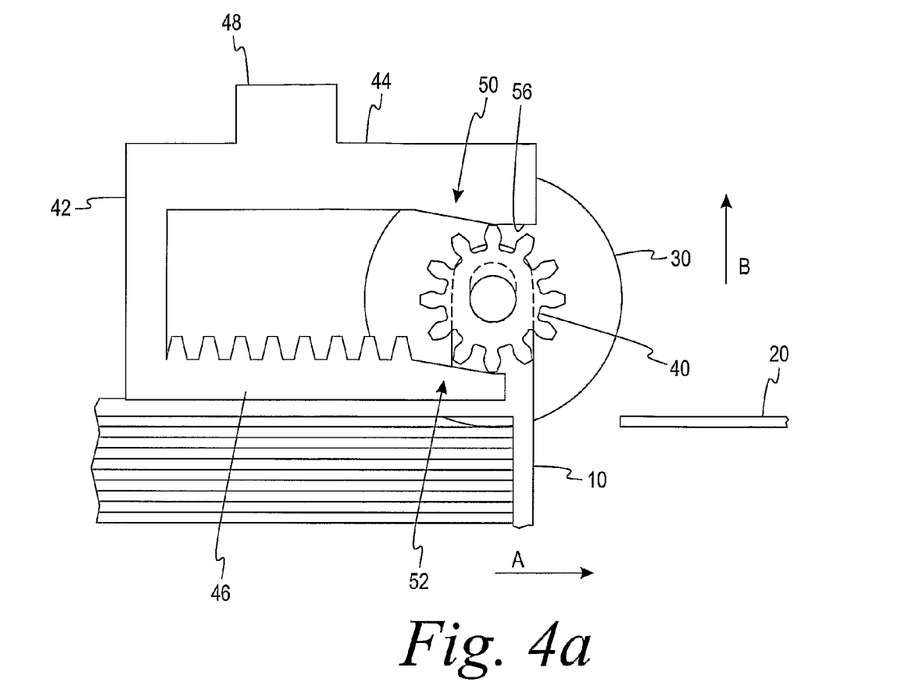
FIG. 4a is a side view of the wheel and gear of FIG. 3a along with a gear rack, where the gear rack is located in a resting position.
Figure 4B:
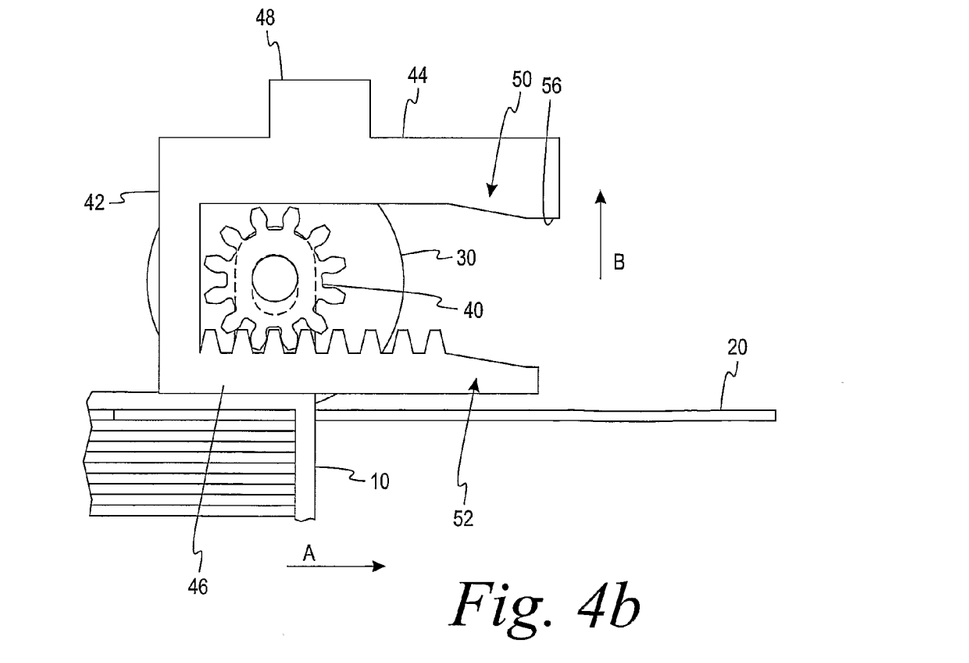
FIG. 4b is a side view of the wheel, gear, and gear rack of FIG. 4a, where the gear rack is located in a dispensing position.

Referring also to FIG. 2, an opening 28 is formed in the walls 12a and 12b. The opening 28 is adapted to allow a portion of the dispensing mechanism 29 to be partially inserted therein. As illustrated in FIG. 2, a wheel 30 is provided within the dispensing mechanism 29. The wheel 30 is adapted to be partially inserted into the opening 28 and to seal the opening 28 from the external environment when the wheel 30 is in its resting position. The wheel 30 is adapted to rotate within the opening 28 as the dispensing mechanism 29 moves from a resting position (FIG. 4a) to a dispensing position (FIG. 4b). The wall 12a is provided with a curved, recessed portion 32 while a pair of extensions 34a,b is each provided with a curved ledge 33. The curvature of both the recessed portion 32 and the curved ledges 33 is adapted to match the curvature of the wheel 30 and allows a greater surface area for the wheel 30 to contact for creating the seal. The wall 12b is provided with a similar curved, recessed portion (not shown) as well.

The pair of extensions 34a,b extends from the exterior surface of the wall 12a. The extensions 34a,b each has an aperture 36a,b, respectively, formed therein. A pin 38 extends from the wheel 30 and is adapted to insert through the aperture 36b in the extension 34b. A second pin (not shown) extends from the opposite side of the wheel 30 and is adapted to insert through the aperture 36a in the extension 34a. The pin 38 is typically longer than the thickness of the aperture 36 and extends from the extension 34b once the pin 38 has been inserted therethrough. The apertures 36a,b are generally circular at the ends and have a flat extension located between the circular ends. As will be explained, the flat extensions allow the wheel 30 to be lifted slightly from the cartridge 10 to allow a test sensor 20 to be dispensed. The generally circular ends allow the pins to rotate within the apertures 36a,b, as will be discussed below.

The pin 38 is adapted to engage a gear 40, as best seen in FIG. 1. Thus, when the gear 40 is rotated, the pin 38 and wheel 30 rotate as well. The dispensing mechanism 29 further comprises a gear rack 42 that is adapted to engage and drive the gear 40. The gear rack 42 comprises a first portion 44 and a second portion 46 located generally parallel to one another. The second portion 46 contains a plurality of teeth that is adapted to mate with the plurality of teeth located on the gear 40. The gear rack 42 is adapted to move from a resting position to a dispensing position and back. As the gear rack 42 moves from the resting position to the dispense position, the teeth of the gear rack 42 and gear 40 engage each other, causing the gear 40 to rotate in a first direction, as illustrated by Arrow C (FIG. 3b). As the gear rack 42 returns to the resting position, the gear 40 is rotated in a second direction, opposite the first. As illustrated in FIG. 1, the first portion 44 of the gear rack 42 includes a slider 48 that extends from the first portion 44. The slider 48 is adapted to allow a test subject to move the gear rack 42 from the resting position to the dispensing position. The wheel 30, gear 40, gear rack 42, and slider 48 of the dispensing mechanism 29 are adapted to dispense a test sensor 20 from the cartridge 10, as will be explained in more detail below with respect to FIGS. 4a-b.

Figure 3A:
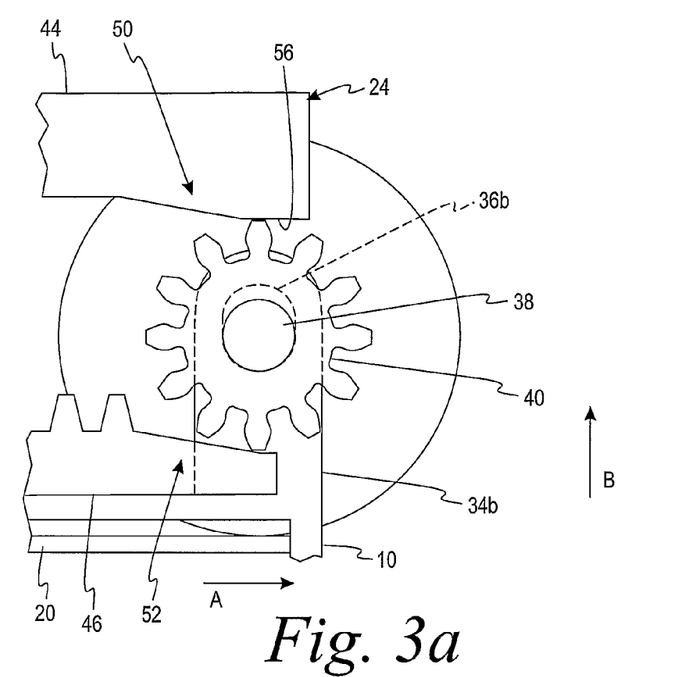
FIG. 3a is a side view of the wheel of FIG. 2 and a gear in a resting position.
Figure 3B:
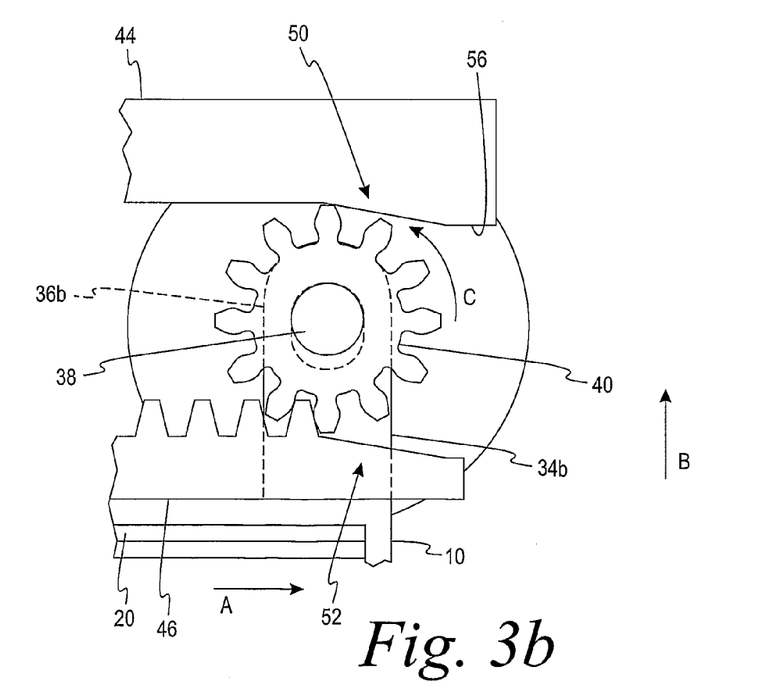
FIG. 3b is a side view of the wheel and the gear of FIG. 3a in a dispensing position.

Referring also to FIGS. 3a-b, a portion of the dispensing mechanism 29 of FIG. 1 is shown in close up. As illustrated, the gear 40 is in the resting position between the first portion 44 and the second portion 46 of the gear rack 42. In this position, the pin 38 extending into (and in some embodiments through) the gear 40 is located in a portion of the aperture 36b nearest the cartridge 10. The gear 40 is placed and maintained in this position by an acclivity 50 on the first portion 44 of the gear rack 42. A matching declivity 52 is provided on the second portion 46 of the gear rack 42 having the same slope as the acclivity 50. The declivity 52 directs the gear away from the cartridge 10 (Arrow B) as the gear rack 42 is moved in the direction of Arrow A. Similarly, the acclivity 50 directs the gear 40 in the direction of the cartridge 10 as the gear rack 42 is moved in the opposite direction as Arrow A. As the gear 40 moves towards the cartridge 10, the pin 38 moves towards the cartridge 10 as well, and thus, towards the portion of the aperture 36b nearest the cartridge 10. A generally flat, sealing portion 56 is located at the end of the acclivity 50 on the first portion 44 of the gear rack 42. The sealing portion 56 causes the wheel 30 to engage the recessed portions and curved ledges—sealing the opening 28. A stop (not shown) may be provided to prevent the gear rack 42 from being moved too far and disengaging the gear 40.

As illustrated in FIG. 3b, as the gear rack 42 is moved in the direction of Arrow A the gear 40 is moved in the direction of Arrow B—away from the cartridge 10. This movement causes the pin 38 to move into a portion of the aperture 36b furthest from the cartridge 10. As the gear rack 42 continues to move in the direction of Arrow A, the teeth of the gear 40 engage the teeth of the gear rack 42 and the gear 40 begins to be rotationally driven in the direction of Arrow C. However, the gear 40 may remain static, or may rotate slightly, prior to engaging the teeth of the gear rack 42 due to the frictional coefficient between the gear 40 and the first and second portions 44, 46 of the gear rack 42.

The rotation of the gear 40—caused by moving the gear rack 42 in the direction of Arrow A—results in the rotation of both the pin 38 and the wheel 30, accordingly. This rotation is utilized to dispense a test sensor 20 from the cartridge 10 as will now be more fully detailed with respect to FIGS. 4a-b. FIG. 4a illustrates the gear rack 42, the gear 40, and the wheel 30 of the dispensing mechanism 29 in the resting position. In this position, the wheel 30 seals the opening 28. As the gear rack 42 is moved in the direction of Arrow A towards the dispensing position (FIG. 4b) the seal is broken as the gear 40 progresses up the declivity 52 of the second portion 46 of the gear rack 42.

As the gear 40 and wheel 30 are moved away from the cartridge 10, the retention plate 22 and springs 24a,b force the test sensors 20 towards the wall 12a, ensuring that one of the test sensors 20 (furthest from the retention plate 22) remains in contact with the wheel 30. Once the wheel 30 has been moved as far away from the cartridge 10 as allowed by the apertures 34a,b (i.e., when the gear 40 reaches the end of the declivity 52 nearest the teeth), a test sensor 20 is capable of being dispensed through the opening 28 in the cartridge 10, as illustrated in FIG. 4b.

Once the opening 28 has been unsealed by moving the gear 40 and wheel 30 away from the cartridge 10, the teeth of the gear rack 42 engage the gear 40 causing both the gear 40 and the wheel 30 to rotate. The rotation of the wheel 30 causes the test sensor 20—which is forced into contact with the wheel 30 by the retention plate 22 and the springs 24a,b—to move laterally in the direction of Arrow A. The test sensor 20 begins to be dispensed through the opening 28 once the gear 40 begins to rotate. Continuing to move the gear rack 42 in the direction of Arrow A further rotates the wheel 30, causing the test sensor 20 to be further dispensed from the cartridge 10. Once the gear 40 has proceeded to the end of the gear rack 42 or alternatively, once the gear rack 42 can no longer be moved in the direction of Arrow A, the gear rack 42 reciprocates back to the resting position. The reciprocation causes the wheel 30 to rotate in the opposite direction, securing the next-adjacent test sensor 20 in its storage position prior to sealing the opening 28.

In one embodiment of the present invention, the wheel 30 is rotated sufficiently to completely eject a single test sensor 20 from the cartridge 10. In this embodiment, once the test sensor 20 has been ejected, the gear rack 42 may not move further in the direction of Arrow A. In another embodiment of the present invention, the wheel 30 is rotated further than is necessary to completely eject a single test sensor 20 from the cartridge.

As should be apparent from the above discussion, after a first test sensor 20 has been dispensed from the cartridge 10, a void is created between the wheel 30 and the next-adjacent test sensor 20. The next-adjacent test sensor 20 is then brought into contact with the wheel 30 by the retention plate 22 and springs 24a,b. In embodiments where the wheel 30 rotates further than is necessary to eject a single test sensor 20, the next-adjacent test sensor 20 may be slightly ejected by the over-rotation. However, as the gear rack 42 moves back to the resting position, the wheel 30 is rotated in the opposite direction and thus, moves the test sensor 20 into its proper storage position. As the gear 40 reaches the acclivity 50 on the first portion 44 of the gear rack 42, both the gear 40 and the wheel 30 are moved towards the cartridge 10 in the opposite direction as Arrow B. Once the wheel 30 reaches the sealing portion 56 of the first portion 44 of the gear rack 42, the wheel 30 is forced into the opening 28 of the cartridge 10 and seals the cartridge 10 from the external environment. As the wheel 30 is forced into the opening 28, the remaining test sensors 20, as well as the retention plate 22, are forced away from the wall 12a and the springs 24a,b are further compressed.

As illustrated in FIG. 1 and FIGS. 3-4, the wheel 30 has a larger diameter than the gear 40 that engages it. Because every rotation of the gear 40 rotates the wheel 30 a full rotation, the distance traveled at the periphery of the wheel 30 is greater than the distance traveled by the gear rack 42 (i.e., the gear driver). Thus, a test subject is required to move the slider 48 a shorter distance than would typically be required to dispense a test sensor. This is particularly beneficial to test subjects with smaller hands, such as children. By adjusting the size of the wheel 30 to the gear 40, the distance the slider 48 is required to move to dispense a test sensor 20 may be varied.

The wheel 30 may be formed from any number of materials capable of generating sufficient friction with the test sensor 20 to cause the test sensor to be dispensed from the cartridge 10. Additionally, it is desirable, though not required, that the wheel 30 be slightly pliable so as to form a tight seal with the curved, recessed portions and ledges of the opening 28, while being able to exert sufficient force on the test sensors 20 to compress the spring mechanism 23 when the dispensing mechanism 29 is in the resting position. For example, the wheel 30 may be made of rubber.

The gear 40 and gear rack 42 may be made of any sufficiently solid material, such that rotation of the gear 40 is achieved when the gear rack 42 is moved from the resting position to the dispensing position. For example, the gear 40 and gear rack 42 may be formed from plastic or metallic materials. It should also be noted that although the gear rack 42 is shown as having teeth on the second portion 46, the teeth could alternatively be provided on the first portion 44 of the gear rack 42.

Figure 5:
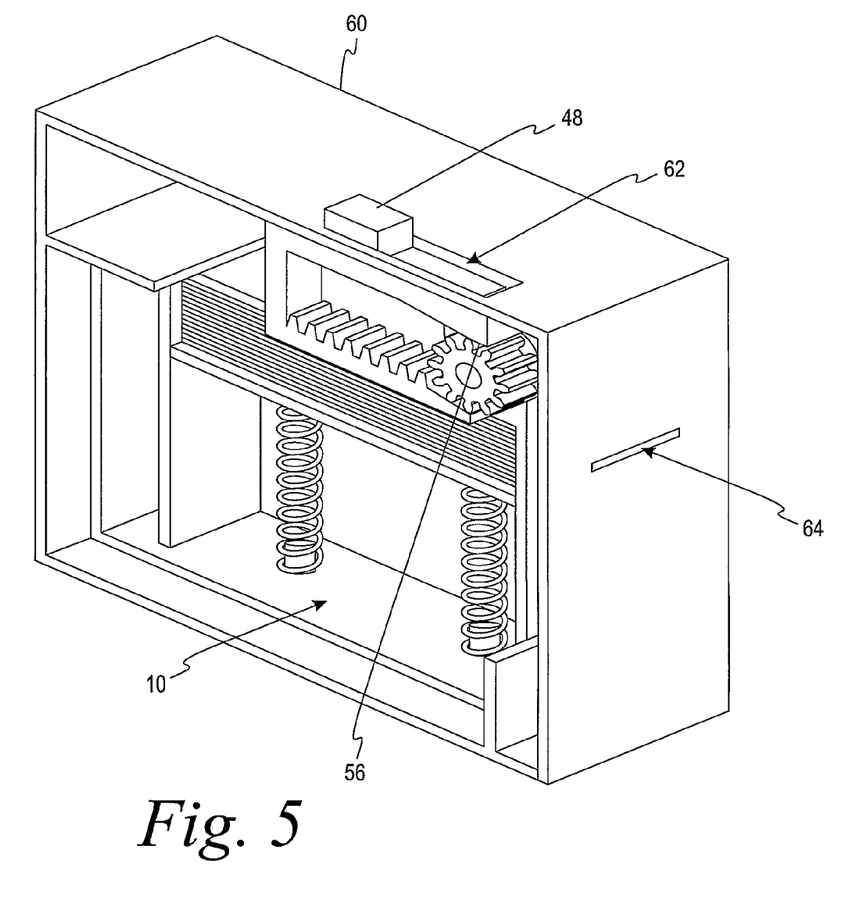
FIG. 5 is a perspective view of the cartridge of FIG. 1 removably inserted into a cartridge casing, according to one embodiment of the present invention.

Turning now to FIG. 5, according to one embodiment of the present invention, the dispensing mechanism 29 and cartridge 10 are adapted to be removably inserted into a cartridge casing 60. The cartridge casing 60 may be adapted to be inserted directly into a meter capable of determining an analyte concentration by analyzing a fluid sample applied to a dispensed test sensor 20. In this embodiment, the cartridge casing 60 includes any necessary attachment mechanisms adapted to engage with an attachment mechanism on or within the meter. Alternatively, the cartridge casing 60 may be used to protect the cartridge 10 and the dispensing mechanism 29 where the device is being used as a stand-alone, test-sensor dispensing cartridge.

The cartridge casing 60 comprises a slider opening 62 and a test-sensor opening 64 formed on the exterior of the cartridge casing 60. The slider opening 62 is adapted to allow a slider 48 to extend therethrough and be accessible to the test subject. The test-sensor opening 64 is adapted to allow a test sensor 20 to be ejected therefrom. Thus, when a test sensor 20 is dispensed from the cartridge 10, the test sensor 20 is at least partially ejected through the test-sensor opening 64 and is able to be grasped by the test subject from outside the cartridge casing 60. The cartridge casing 60 may include various electrical components for analyzing an analyte concentration in a body fluid sample, as is well known in the art.

Figure 6:
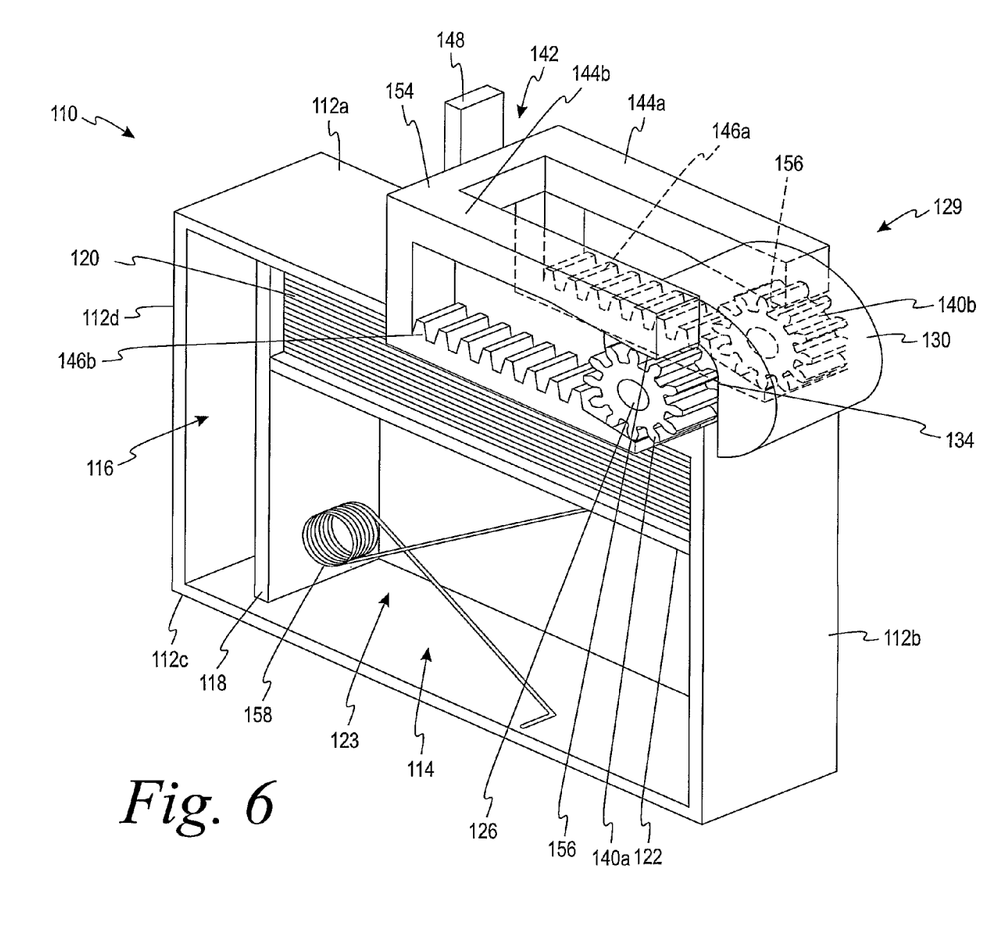
FIG. 6 is a perspective view of a cartridge adapted to contain and dispense a plurality of test sensors, according to another embodiment of the present invention.

Turning now to FIG. 6, a test-sensor cartridge 110 is illustrated, according to another embodiment of the present invention. The various components illustrated in FIG. 6 interact and function in the same manner as described above with respect to FIGS. 1-4b. The cartridge 110 includes a plurality of walls 112a-d and a divide 118 forming a desiccant cavity 116 and a central cavity 114 that contains a plurality of test sensors 120. The central cavity also includes a retention plate 122 and spring mechanism 123 for biasing the retention plate 122 in the direction of the wall 112a. A dispensing mechanism 129 is provided near an opening (not shown) that is sealed by a wheel 130 having posts 126 that each extend through an aperture (not shown) formed in each extension 134.

The spring mechanism 123 includes a torsion spring 158 located between the retention plate 122 and the wall 112c. The torsion spring 158 causes the retention plate 122 to engage the test sensors 120 and bring them proximate to the interior surface (not shown) of the wall 112a.

The dispensing mechanism 129 includes the wheel 130 located between a plurality of gears 140a,b with at least one gear 140a,b being located on each side of the wheel 130. The gears 140a,b engage the wheel 130 via posts 126 extending from the wheel 130. The dispensing mechanism 129 further includes a gear rack 142 adapted to engage each of the plurality of gears 140a,b. The gear rack 142 includes a plurality of first portions 144a,b and a plurality of second portions 146a,b. The plurality of second portions 146a,b each contains a plurality of teeth that is adapted to mate with the plurality of teeth located on the gears 140a,b. The gear rack 142 is adapted to move from a resting position to a dispensing position and back. As the gear rack 142 moves from the resting position to the dispense position, the teeth of the gear rack 142 and gears 140a,b engage each other, causing the gears 140a,b and wheel 130 to rotate. A slider 148 is attached to a support 154 from with the first portions 144a,b and second portions 146a,b of the gear rack 142 extend.

Utilizing a dual-drive type dispensing mechanism 129 further assists with the sealing of the cartridge 110. For example, in a single-drive type dispensing mechanism 29 (illustrated in FIGS. 1-5) when the gear rack 42 is moved to the resting position, the acclivity 50 and sealing portion 56 force the single gear 40 and thus, the wheel 30, towards the cartridge 10. However, because only one side of the wheel 30 is being forced in the direction of the cartridge 10, the wheel 30 tends to tilt slightly in the direction of the gear 40. This creates a tighter seal on the gear side of the wheel 30 than on the non-gear side. Though the acclivity 50 and sealing portion 56 are of sufficient slope to effectively seal the cartridge 10, a dual-drive type dispensing mechanism 129 allows a pair of sealing portions 150, located on each first portion 144a,b of the gear rack 142 to assist in the sealing of the cartridge 110. Because both gears 140a,b are being forced in the direction of the cartridge 110, an even tighter seal is formed because the wheel 30 is evenly pressed towards the cartridge 110.

Figure 7:
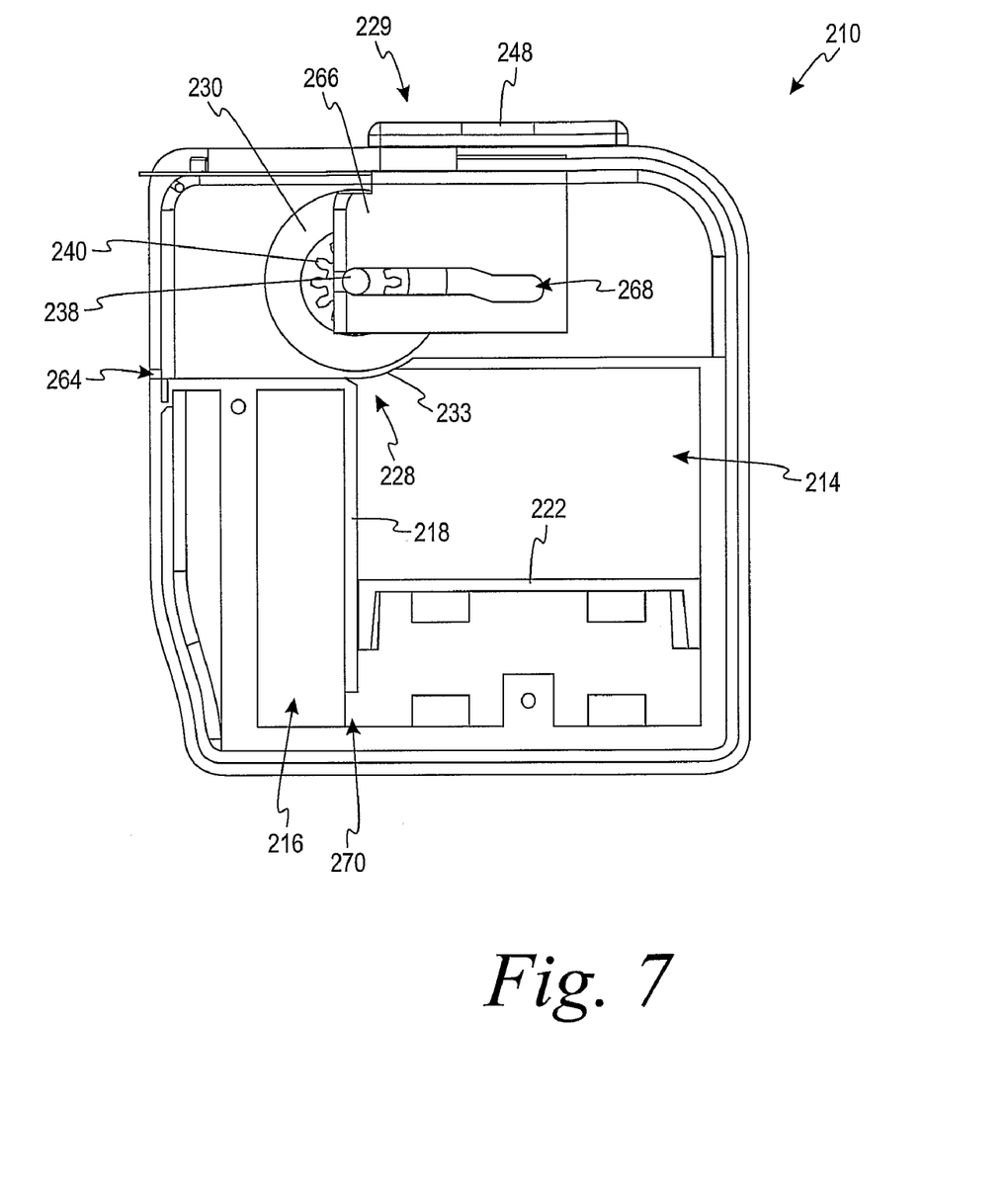
FIG. 7 is a side view of a cartridge adapted to contain and dispense a plurality of test sensors, according to yet another embodiment of the present invention.
Figure 8:
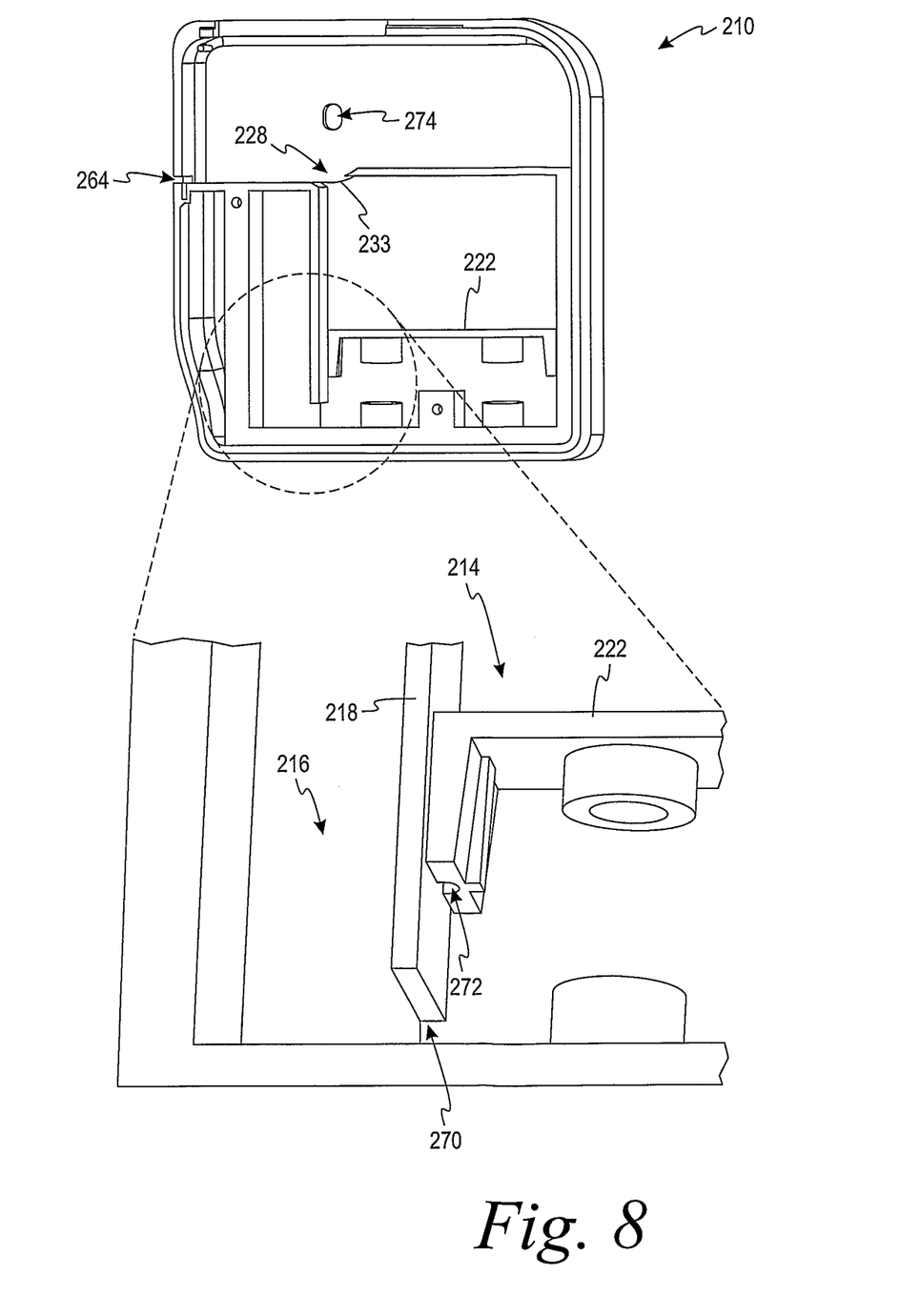
FIG. 8 is a perspective side view of a cartridge adapted to contain a plurality of test sensors, according to still another embodiment of the present invention.

Turning now to FIGS. 7-8, a cartridge 210 adapted to contain and dispense a plurality of test sensors is illustrated, according to yet another embodiment of the present invention. The cartridge 210 forms a central cavity 214 adapted to contain a plurality of test sensors and a desiccant cavity 216 adapted to contain a desiccant. The central cavity 214 and the desiccant cavity 216 are separated by a divide 218 having an air gap 270 located at at least one end of the divide 218. The central cavity 214 includes a retention plate 222 having a vent 272 located along the divide 218. The desiccant in the desiccant cavity 216 is allowed to extract moisture from the air within the central cavity 214 as the desiccant is in communication with the air within the central cavity 214 via the air gap 270 and the vent 272.

A dispensing mechanism 229 is located within the cartridge 210 for dispensing the test sensors from the central cavity 214 via a test-sensor opening 264 formed in the cartridge 210. The dispensing mechanism 229 includes a wheel 230 adapted to individually engage and move the test sensors. The wheel 230 is further adapted to seal an opening 228 when the dispensing mechanism 229 is in a resting position. A curved ledge 233 is provided to increase the surface area of the seal by the wheel 230. The wheel 230 includes a gear 240 or is operatively connected to the gear 240 via a pin 238. The dispensing mechanism 229 further includes a slide rail 266 having a slot 268 formed therein. The pin 238 is adapted to at least partially extend into (or through) the slot 268. The slot 268 formed in the slide rail 266 is adapted to restrict the vertical movement (i.e., toward and away from the opening 228) of the wheel 230 while allowing the lateral movement (i.e., toward and away from the test-sensor opening 264) of the dispensing mechanism 229. The pin 238 is further adapted to at least partially extend into (or through) a oval pocket 274. The oval pocket 274 is adapted to restrict the lateral movement of the wheel, while allowing the vertical movement of the wheel.

The dispensing mechanism 229 includes a gear rack (not shown) formed along an inner portion of the slide rail 266. The dispensing mechanism 229 further includes a slider 248 that is externally-accessible from the cartridge 210 by a user.

Figure 9:
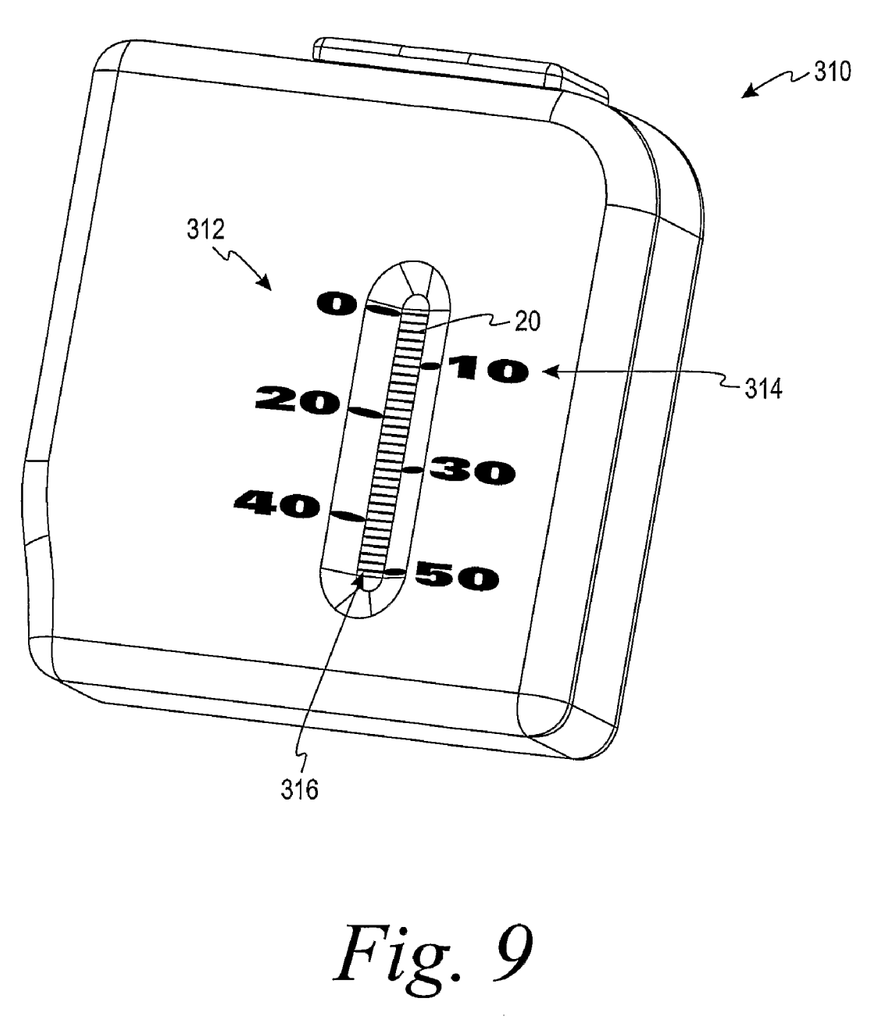
FIG. 9 is a perspective view of a cartridge adapted to contain and dispense a plurality of test sensors, according to one embodiment of the present invention

Referring now to FIG. 9, a test-sensor indicator 312 for a cartridge 310 adapted to contain and dispense a plurality of test sensors is illustrated, according to one embodiment of the present invention. The test-sensor indicator 312 includes one or more indicators 314 located proximate to a window 316. The window 316 allows a user to visibly identify the test sensors 22 within the cartridge 310. Once the test sensors 22 have been visibly identified, the user can reference the one or more indicators 314 to determine the number, percentage, days, etc. of test strips remaining. In the illustrated example, the one or more indicators 314 represent the number of test sensors 22 remaining within the cartridge 310.

Alternative Embodiment A

A dispensing mechanism for ejecting a test sensor from a cartridge opening formed in a cartridge containing a plurality of test sensors, the dispensing mechanism comprising:

a gear rack including a first portion and a second portion located generally parallel to one another, the second portion of the gear rack including a first plurality of teeth;

a gear including a second plurality of teeth, the second plurality of teeth being adapted to be engaged by the first plurality of teeth upon movement of the gear rack; and a wheel operatively engaged by the gear, the wheel being adapted to dispense the test sensor from the cartridge opening and to seal the cartridge opening, wherein movement of the gear rack in a first direction causes the gear to rotate causing the wheel to rotate, the rotation of the wheel dispensing the test sensor through the cartridge opening.

Alternative Embodiment B

The dispensing mechanism of Alternative Embodiment A wherein the first portion of the gear rack includes an acclivity and the second portion of the gear rack includes a complimentary declivity.

Alternative Embodiment C

The dispensing mechanism of Alternative Embodiment B wherein a sealing portion extends from the acclivity, the sealing portion being adapted to place the gear in a resting position.

Alternative Embodiment D

The dispensing mechanism of Alternative Embodiment C wherein the wheel seals the cartridge opening when the gear is placed in the resting position.

Alternative Embodiment E

The dispensing mechanism of Alternative Embodiment B wherein the declivity causes the wheel to move away from the cartridge so as to expose a portion of the cartridge opening, the test sensor being dispensed through the exposed portion of the cartridge opening.

Alternative Embodiment F

The dispensing mechanism of Alternative Embodiment A wherein the wheel is made of rubber.

Alternative Embodiment G

The dispensing mechanism of Alternative Embodiment A wherein the diameter of the wheel is greater than the diameter of the gear.

Alternative Embodiment H

The dispensing mechanism of Alternative Embodiment G wherein the test sensor is moved further in the first direction than the gear rack when the gear rack is moved in the first direction.

Alternative Embodiment I

The dispensing mechanism of Alternative Embodiment A wherein the movement of the gear rack in the first direction moves the test sensor in the first direction.

Alternative Embodiment J

The dispensing mechanism of Alternative Embodiment A further comprising a slider located on the gear rack, the slider being adapted to move the gear rack between a resting position and a dispensing position.

Alternative Embodiment K

A cartridge comprising:

a plurality of walls forming at least one cavity therein, the cavity being adapted to contain a plurality of test sensors, the plurality of test sensors being adapted to assist in the determination of a concentration of an analyte in a fluid sample, at least one of the plurality of walls having an opening adapted to allow a test sensor to be dispensed therefrom;

a dispensing mechanism adapted to dispense a test sensor through the opening, the dispensing mechanism including, (i) a gear rack including a first portion and a second portion located generally parallel to one another, the first portion of the gear rack including a first plurality of teeth, (ii) a gear including a second plurality of teeth, the second plurality of teeth being adapted to be engaged by the first plurality of teeth upon movement of the gear rack, and (iii) a wheel operatively engaged by the gear, the wheel being adapted to dispense the test sensor from the opening and to seal the opening;

a retention plate located in the at least one cavity, the retention plate being adapted to engage at least one of the plurality of test sensors; and a spring mechanism adapted to engage the retention plate, the spring mechanism exerting a force on the retention place in the direction of the wheel, wherein the spring mechanism and the retention plate force at least one of the test sensors into contact with a portion of the wheel of the dispensing mechanism.

Alternative Embodiment L

The cartridge of Alternative Embodiment K wherein the at least one cavity is two cavities separated by a divide, the two cavities being in communication with each other, the first cavity containing the plurality of test strips and the second cavity containing a desiccant.

Alternative Embodiment M

The cartridge of Alternative Embodiment K wherein the walls of the cartridge have only one opening formed therein.

Alternative Embodiment N

The cartridge of Alternative Embodiment K wherein the spring mechanism includes a plurality of springs extending between one of the plurality of walls and the retention plate.

Alternative Embodiment O

The cartridge of Alternative Embodiment K wherein the spring mechanism includes a torsion spring located between one of the plurality of walls and the retention plate.

Alternative Embodiment P

A dispensing mechanism for ejecting a test sensor from a cartridge opening formed in a cartridge containing a plurality of test sensors, the dispensing mechanism comprising:

a plurality of gears, each of the plurality of gears including a plurality of teeth;

a wheel operatively engaged by the plurality of gears, the wheel being adapted to dispense the test sensor from the cartridge opening and to seal the cartridge opening; and a gear rack including a plurality of first portions and a plurality of second portion located generally parallel to one another, at least one of the plurality of first and second portions being located on opposite sides of the wheel, the plurality of second portions of the gear rack each including a plurality of teeth, the plurality of teeth on the plurality of second portions being adapted to engage the plurality of teeth on the plurality of gears, wherein movement of the gear rack in a first direction causes the plurality of gears to rotate causing the wheel to rotate, the rotation of the wheel dispensing the test sensor through the cartridge opening.

Alternative Embodiment Q

The dispensing mechanism of Alternative Embodiment P wherein the first portion of the gear rack includes an acclivity and the second portion of the gear rack includes a complimentary declivity.

Alternative Embodiment R

The dispensing mechanism of Alternative Embodiment Q wherein a sealing portion extends from the acclivity, the sealing portion being adapted to place the gear in a resting position.

Alternative Embodiment S

The dispensing mechanism of Alternative Embodiment R wherein the wheel seals the cartridge opening when the gear is placed in the resting position.

Alternative Embodiment T

The dispensing mechanism of Alternative Embodiment P wherein the diameter of the wheel is greater than the diameter of the gear.

Alternative Embodiment U

The dispensing mechanism of Alternative Embodiment T wherein the test sensor is moved further in the first direction than the gear rack when the gear rack is moved in the first direction.

Alternative Embodiment V

The dispensing mechanism of Alternative Embodiment P wherein gear rack includes a support from which the plurality of first and second portions extend.

Alternative Embodiment W

The dispensing mechanism of Alternative Embodiment V further comprising a slider located on the support of the gear rack, the slider being adapted to move the gear rack between a resting position and a dispensing position.

Alternative Embodiment X

A cartridge comprising:

a plurality of walls forming at least one cavity therein, the cavity being adapted to contain a plurality of test sensors, the plurality of test sensors being adapted to assist in the determination of a concentration of an analyte in a fluid sample, at least one of the plurality of walls having an opening adapted to allow a test sensor to be dispensed therefrom;

a dispensing mechanism adapted to dispense a test sensor through the opening, the dispensing mechanism including, (i) a plurality of gears, each of the plurality of gears including a plurality of teeth, (ii) a wheel operatively engaged by the plurality of gears, the wheel being adapted to dispense the test sensor from the cartridge opening and to seal the cartridge opening, and (iii) a gear rack including a plurality of first portions and a plurality of second portion located generally parallel to one another, at least one of the plurality of first and second portions being located on opposite sides of the wheel, the plurality of second portions of the gear rack each including a plurality of teeth, the plurality of teeth on the plurality of second portions being adapted to engage the plurality of teeth on the plurality of gears;

a retention plate located in the at least one cavity, the retention plate being adapted to engage at least one of the plurality of test sensors; and a spring mechanism adapted to engage the retention plate, the spring mechanism exerting a force on the retention place in the direction of the wheel, wherein the spring mechanism and the retention plate force at least one of the test sensors into contact with a portion of the wheel of the dispensing mechanism.

Alternative Embodiment Y

The cartridge of Alternative Embodiment X wherein the at least one cavity is two cavities separated by a divide, the two cavities being in communication with each other, the first cavity containing the plurality of test strips and the second cavity containing a desiccant.

Alternative Embodiment Z

The cartridge of Alternative Embodiment X wherein the walls of the cartridge have only one opening formed therein.

Alternative Embodiment AA

The cartridge of Alternative Embodiment X wherein the spring mechanism includes a plurality of springs extending between one of the plurality of walls and the retention plate.

Alternative Embodiment BB

The cartridge of Alternative Embodiment X wherein the spring mechanism includes a torsion spring located between one of the plurality of walls and the retention plate.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A dispensing mechanism for ejecting a test sensor from a cartridge opening formed in a cartridge containing a plurality of test sensors, the dispensing mechanism comprising:
   a gear rack including a first portion and a second portion located generally parallel to one another, the second portion of the gear rack including a first plurality of teeth;
   a gear including a second plurality of teeth, the second plurality of teeth being adapted to be engaged by the first plurality of teeth upon movement of the gear rack; and
   a wheel operatively engaged by the gear, the wheel being adapted to dispense the test sensor from the cartridge opening and to seal the cartridge opening,
   wherein movement of the gear rack in a first direction causes the gear to rotate causing the wheel to rotate, the rotation of the wheel dispensing the test sensor through the cartridge opening.

2. The dispensing mechanism of claim 1, wherein the first portion of the gear rack includes an acclivity and the second portion of the gear rack includes a complimentary declivity.

3. The dispensing mechanism of claim 2, wherein a sealing portion extends from the acclivity, the sealing portion being adapted to place the gear in a resting position.

4. The dispensing mechanism of claim 3, wherein the wheel seals the cartridge opening when the gear is placed in the resting position.

5. The dispensing mechanism of claim 2, wherein the declivity causes the wheel to move away from the cartridge so as to expose a portion of the cartridge opening, the test sensor being dispensed through the exposed portion of the cartridge opening.

6. The dispensing mechanism of claim 1, wherein the wheel comprises rubber.

7. The dispensing mechanism of claim 1, wherein the diameter of the wheel is greater than the diameter of the gear.

8. The dispensing mechanism of claim 7, wherein the test sensor is moved further in the first direction than the gear rack when the gear rack is moved in the first direction.

9. The dispensing mechanism of claim 1, wherein the movement of the gear rack in the first direction moves the test sensor in the first direction.

10. The dispensing mechanism of claim 1, further comprising a slider located on the gear rack, the slider being adapted to move the gear rack between a resting position and a dispensing position.

11. A cartridge comprising:
    a plurality of walls forming at least one cavity therein, the cavity being adapted to contain a plurality of test sensors, the plurality of test sensors being adapted to assist in the determination of a concentration of an analyte in a fluid sample, at least one of the plurality of walls forming an opening adapted to allow a test sensor to be dispensed therefrom;
    a dispensing mechanism adapted to dispense a test sensor through the opening, the dispensing mechanism including,
    (i) a gear rack including a first portion and a second portion located generally parallel to one another, the second portion of the gear rack including a first plurality of teeth,
    (ii) a gear including a second plurality of teeth, the second plurality of teeth being adapted to be engaged by the first plurality of teeth upon movement of the gear rack, and
    (iii) a wheel operatively engaged by the gear, the wheel being adapted to dispense the test sensor from the opening and to seal the opening;
    a retention plate located in the at least one cavity, the retention plate being adapted to engage at least one of the plurality of test sensors; and
    a spring mechanism adapted to engage the retention plate, the spring mechanism exerting a force on the retention plate in the direction of the wheel,
    wherein the spring mechanism and the retention plate force at least one of the test sensors into contact with a portion of the wheel of the dispensing mechanism.

12. The cartridge of claim 11, wherein the at least one cavity is two cavities separated by a divide, the two cavities being in communication with each other, the first cavity containing the plurality of test strips and the second cavity containing a desiccant.

13. The cartridge of claim 11, wherein the walls of the cartridge form only one opening therein.

14. The cartridge of claim 11, wherein the spring mechanism includes a plurality of springs extending between one of the plurality of walls and the retention plate.

15. The cartridge of claim 11, wherein the spring mechanism includes a torsion spring located between one of the plurality of walls and the retention plate.

16. A dispensing mechanism for ejecting a test sensor from a cartridge opening formed in a cartridge containing a plurality of test sensors, the dispensing mechanism comprising:
    a plurality of gears, each of the plurality of gears including a plurality of teeth;
    a wheel operatively engaged by the plurality of gears, the wheel being adapted to dispense the test sensor from the cartridge opening and to seal the cartridge opening; and
    a gear rack including a plurality of first portions and a plurality of second portions located generally parallel to one another, at least one of the plurality of first and second portions being located on opposite sides of the wheel, the plurality of second portions of the gear rack each including a plurality of teeth, the plurality of teeth on the plurality of second portions being adapted to engage the plurality of teeth on the plurality of gears,
    wherein movement of the gear rack in a first direction causes the plurality of gears to rotate causing the wheel to rotate, the rotation of the wheel dispensing the test sensor through the cartridge opening.

17. The dispensing mechanism of claim 16, wherein the first portion of the gear rack includes an acclivity and the second portion of the gear rack includes a complimentary declivity.

18. The dispensing mechanism of claim 17, wherein a sealing portion extends from the acclivity, the sealing portion being adapted to place the gear in a resting position.

19. The dispensing mechanism of claim 18, wherein the wheel seals the cartridge opening when the gear is placed in the resting position.

20. The dispensing mechanism of claim 16, wherein the diameter of the wheel is greater than the diameter of the gear.

21. The dispensing mechanism of claim 20, wherein the test sensor is moved further in the first direction than the gear rack when the gear rack is moved in the first direction.

22. A cartridge comprising:
    a plurality of walls forming at least one cavity therein, the cavity being adapted to contain a plurality of test sensors, the plurality of test sensors being adapted to assist in the determination of a concentration of an analyte in a fluid sample, at least one of the plurality of walls having an opening adapted to allow a test sensor to be dispensed therefrom;

a dispensing mechanism adapted to dispense a test sensor through the opening, the dispensing mechanism including,
- (i) a plurality of gears, each of the plurality of gears including a plurality of teeth,
- (ii) a wheel operatively engaged by the plurality of gears, the wheel being adapted to dispense the test sensor from the cartridge opening and to seal the cartridge opening, and
- (iii) a gear rack including a plurality of first portions and a plurality of second portions located generally parallel to one another, at least one of the plurality of first and second portions being located on opposite sides of the wheel, the plurality of second portions of the gear rack each including a plurality of teeth, the plurality of teeth on the plurality of second portions being adapted to engage the plurality of teeth on the plurality of gears;

a retention plate located in the at least one cavity, the retention plate being adapted to engage at least one of the plurality of test sensors; and a spring mechanism adapted to engage the retention plate, the spring mechanism exerting a force on the retention plate in the direction of the wheel, wherein the spring mechanism and the retention plate force at least one of the test sensors into contact with a portion of the wheel of the dispensing mechanism.

23. The cartridge of claim 22, wherein the at least one cavity is two cavities separated by a divide, the two cavities being in communication with each other, the first cavity containing the plurality of test strips and the second cavity containing a desiccant.

24. The cartridge of claim 22, wherein the walls of the cartridge have only one opening formed therein.

25. A method of dispensing a test sensor, the method comprising the acts of:

providing a container, the container including a plurality of walls forming at least one cavity therein, the cavity containing a plurality of test sensors, the plurality of test sensors being adapted to assist in the determination of a concentration of an analyte in a fluid sample, at least one of the plurality of walls forming an opening adapted to allow a test sensor to be dispensed therefrom;

providing a dispensing mechanism including
- (i) a gear rack including a first portion and a second portion located generally parallel to one another, the second portion of the gear rack including a first plurality of teeth,
- (ii) a gear including a second plurality of teeth, the second plurality of teeth being adapted to be engaged by the first plurality of teeth upon movement of the gear rack, and
- (iii) a wheel operatively engaged by the gear;

moving the wheel from a position of sealing the opening;

dispensing a test sensor from the container through the opening after the wheel has been moved from the position of sealing the opening.

26. The method of claim 25 wherein dispensing of the test sensor including the wheel contacting the test sensor and assisting in moving the test sensor through the opening.

27. A method using a cartridge comprising:

providing a container, the container including a plurality of walls forming at least one cavity therein, the cavity being adapted to contain a plurality of test sensors, the plurality of test sensors being adapted to assist in the determination of a concentration of an analyte in a fluid sample, at least one of the plurality of walls forming an opening adapted to allow a test sensor to be dispensed therefrom;

providing a dispensing mechanism including
- (i) a plurality of gears, each of the plurality of gears including a plurality of teeth,
- (ii) a wheel operatively engaged by the plurality of gears, the wheel being adapted to dispense the test sensor from the cartridge opening and to seal the cartridge opening, and
- (iii) a gear rack including a plurality of first portions and a plurality of second portions located generally parallel to one another, at least one of the plurality of first and second portions being located on opposite sides of the wheel, the plurality of second portions of the gear rack each including a plurality of teeth, the plurality of teeth on the plurality of second portions being adapted to engage the plurality of teeth on the plurality of gears;

moving the wheel from a position of sealing the opening;

dispensing a test sensor from the container through the opening after the wheel has been moved from the position of sealing the opening.

28. The method of claim 27 wherein dispensing of the test sensor including the wheel contacting the test sensor and assisting in moving the test sensor through the opening.

* * * * *